United States Patent
Zhao

(10) Patent No.: US 7,704,488 B2
(45) Date of Patent: *Apr. 27, 2010

(54) DENDRITIC AND STAR-SHAPED CONTRAST AGENTS FOR MEDICAL DEVICES AND BIOABSORBABLE RADIOPAQUE BULK MATERIAL AND METHOD FOR PRODUCING SAME

(75) Inventor: Jonathon Z. Zhao, Belle Mead, NJ (US)

(73) Assignee: Cordis Corporation, Miami Lakes, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/050,996

(22) Filed: Mar. 19, 2008

(65) Prior Publication Data

US 2008/0177102 A1 Jul. 24, 2008

Related U.S. Application Data

(63) Continuation of application No. 11/368,688, filed on Mar. 6, 2006, now abandoned.

(60) Provisional application No. 60/662,957, filed on Mar. 18, 2005.

(51) Int. Cl.
 *A61K 49/04* (2006.01)
(52) U.S. Cl. .................................................. 424/9.4
(58) Field of Classification Search ............... 424/1.11, 424/9.37, 9.4, 9.45
 See application file for complete search history.

(56) References Cited

U.S. PATENT DOCUMENTS

| 4,665,771 A | 5/1987 | Mitchell |
| 4,665,906 A | 5/1987 | Jervis |
| 4,733,665 A | 3/1988 | Palmaz |
| 4,925,445 A | 5/1990 | Sakamoto et al. |
| 4,935,019 A | 6/1990 | Papp, Jr. |
| 5,632,771 A | 5/1997 | Boatman et al. |
| 5,709,846 A | 1/1998 | Lem et al. |
| 5,725,572 A | 3/1998 | Lam et al. |
| 5,741,327 A | 4/1998 | Frantzen |
| 5,756,066 A | 5/1998 | Nitecki et al. |
| 5,800,526 A | 9/1998 | Anderson et al. |
| 6,022,374 A | 2/2000 | Imran |
| 6,475,477 B1 | 11/2002 | Kohn et al. |

OTHER PUBLICATIONS

European Search Report dated Jul. 20, 2006 for Appln. No. 06251428.6-2107.
European Search Report dated Nov. 3, 2008 for Appln. No. 08013982.7-2103.
European Search Report dated Nov. 3, 2008 for Appln. No. 08013983.5-2103.
European Search Report dated Oct. 11, 2006 for Appln. No. 06251428.6-2103.

*Primary Examiner*—Michael G Hartley
*Assistant Examiner*—Jagadishwar R Samala

(57) ABSTRACT

In accordance with the present invention, a high intensity radiopaque contrast agent is disclosed. The agent may be coated on or incorporated within bulk materials, which may then be subsequently utilized to fabricate a radiopaque medical device. Primary effects through chemistry include higher radiopaque concentrations per unit weight of the radiopaque element or agent. Secondary effects include selective placement of the radiopaque elements which may further enhance the radiopacity of the device with reduced requirements of the radiopaque agent. Such a radiopaque contrast agent may be produced in various forms such as a dendrimer and/or incorporated as the end groups of polymeric chain. In addition one can incorporate biological and/or pharmaceutical agents in combination with the present invention.

5 Claims, 14 Drawing Sheets

Figure 2.
(a).
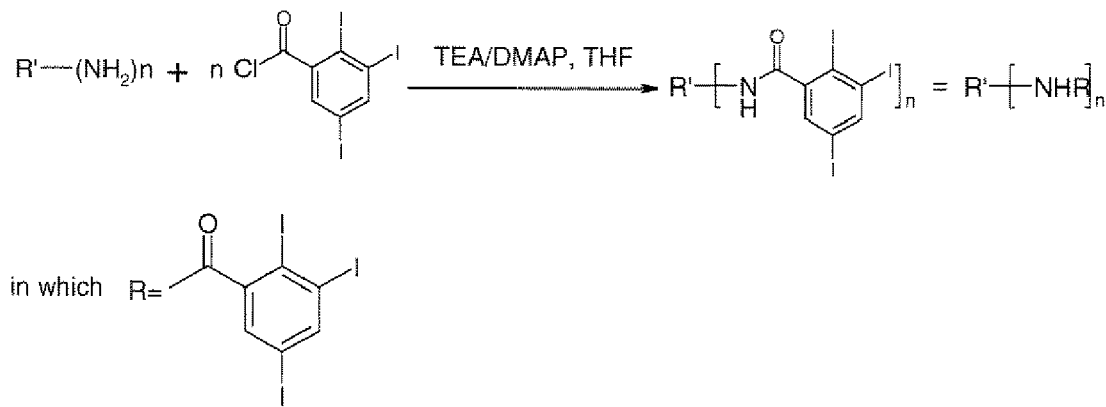
(b).
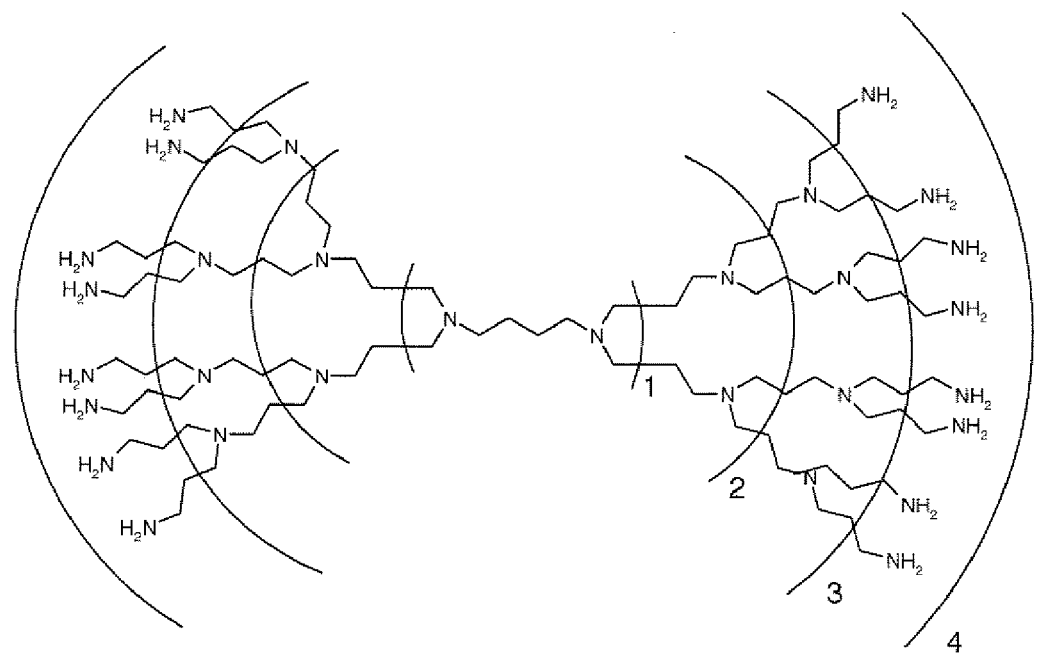

Figure 3 Level 1 of dendritic iodine radiopaque contrast agent, in which the dendrimer has n=2 NHR radiopaque contrast moieties (6 iodine atoms).
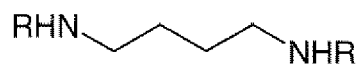
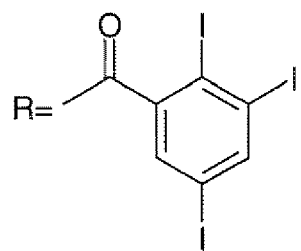

Figure 4. Level 2 dendritic iodine contrast agent
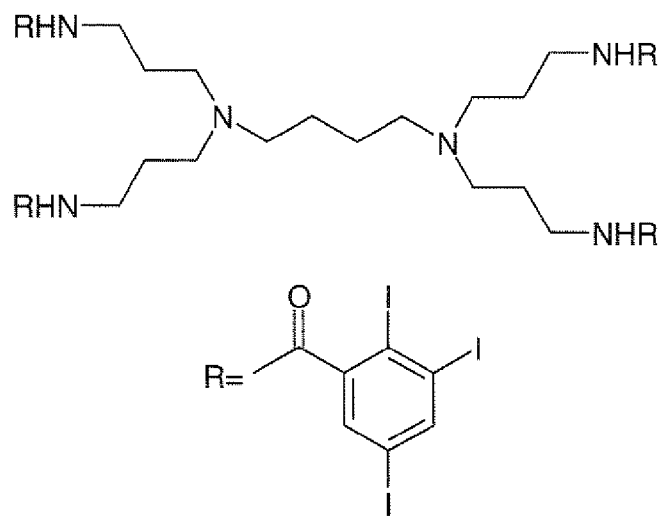
In which the dendrimer has n=4 NHR radiopaque contrast moieties (12 iodine molecules)

Figure 5. Level 3 dendritic iodine contrast agent
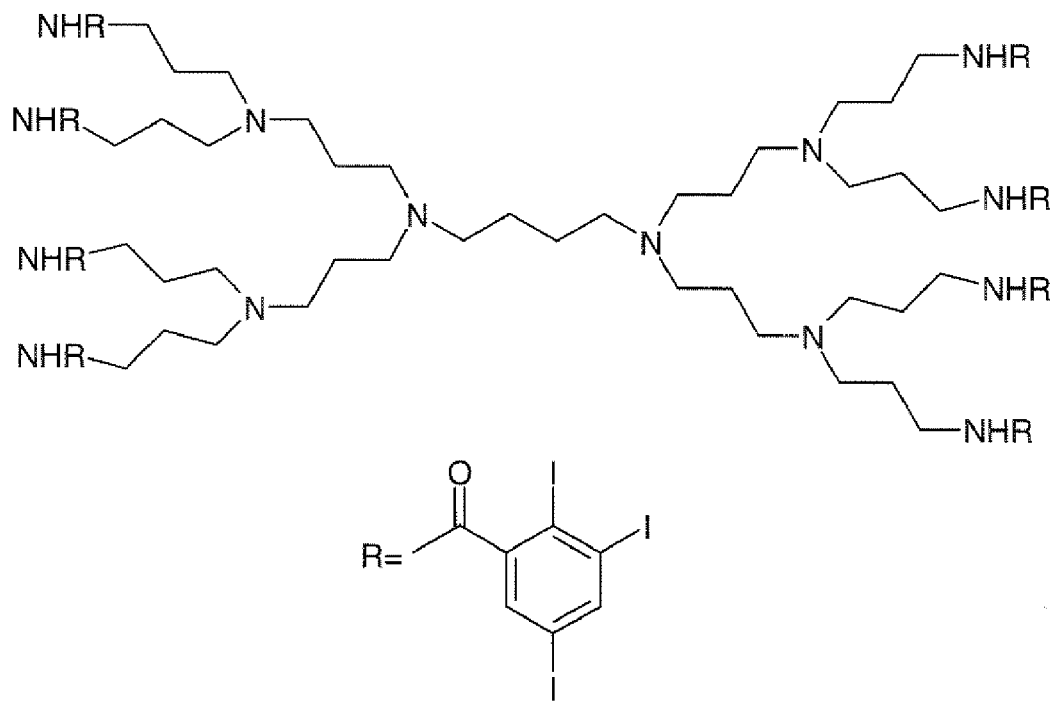
In which the dendrimer has n=8 NHR radiopaque contrast moieties (24 iodine atoms)

Figure 6. Level 4 dendritic iodine contrast agent
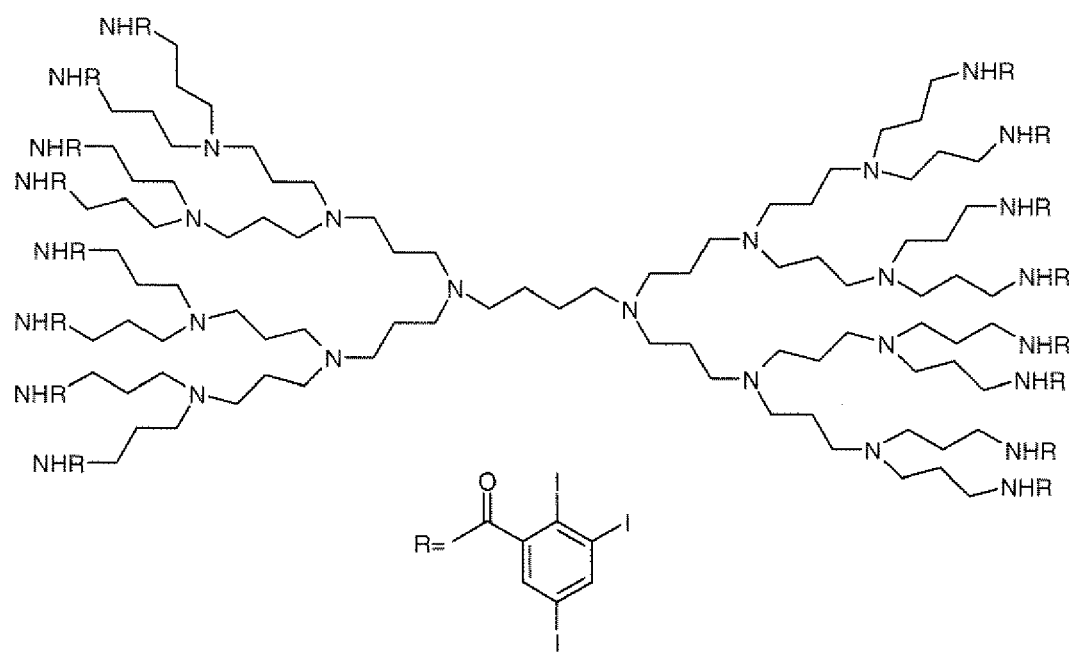
In which the dendrimer has n=16 NHR radiopaque contrast moieties (48 iodine atoms)

50 m=1,2,3;
n=0,1,2; and
m+n=3

Figure 9. Deprotection of Fmoc protected initiator.

Figure 10 Transformation of amine end-capped initiator to a carboxyl end-capped high iodine functional moiety Figure 12
A.
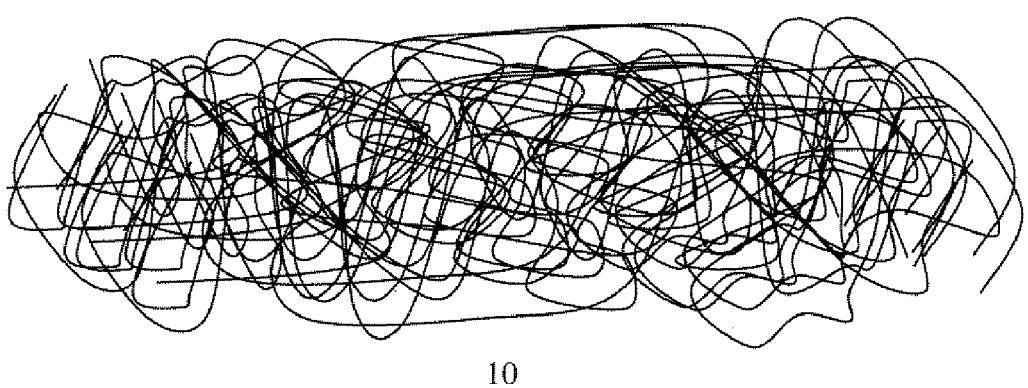
10
B.
11

GA　　　CL　　　DO　　　TMC

DENDRITIC AND STAR-SHAPED CONTRAST AGENTS FOR MEDICAL DEVICES AND BIOABSORBABLE RADIOPAQUE BULK MATERIAL AND METHOD FOR PRODUCING SAME

CROSS REFERENCE TO RELATED APPLICATIONS

This is a continuation of U.S. patent application Ser. No. 11/368,688 filed on Mar. 6, 2006 now abandoned which claims priority under 35 U.S.C. § 119(e) of U.S. Provisional Patent Application No. 60/662,957 filed on Mar. 18, 2005.

FIELD OF THE INVENTION

The present invention relates to intravascular devices used in medical treatment and procedures. More specifically, the present invention relates to a new class of organic high intensity X-ray contrast agents suitable for enhancing the imaging of medical devices, particularly polymeric medical devices and polymeric coatings being fabricated from a polymer with the contrast agent dispersed within, conjugated at one or both ends of the polymers, as well as the method of manufacture of such materials and devices.

DISCUSSION OF THE RELATED ART

Recently, transluminal prostheses have been widely used in the medical arts for implantation in blood vessels, biliary ducts, or other similar organs of living body. These prostheses are commonly known as stents and are used to maintain, open, or dilate tubular structures. An example of a commonly used stent is given in U.S. Pat. No. 4,733,665 filed by Palmaz on Nov. 7, 1985, which is hereby incorporated herein by reference. Such stents are often referred to as balloon expandable stents. Typically the stent is made from a solid tube of stainless steel, although other metallic materials have been utilized. Thereafter, a series of cuts are made in the wall of the stent. The stent has a first smaller diameter, which permits the stent to be delivered through the human vasculature by being crimped onto a balloon catheter. The stent also has a second, expanded diameter, upon application of a radially, outwardly directed force, by the balloon catheter, from the interior of the tubular shaped member.

However, one concern with such stents is that they are often impractical for use in some vessels such as the carotid artery. The carotid artery is easily accessible from the exterior of the human body, and is close to the surface of the skin. A patient having a balloon expandable stent made from stainless steel or the like, placed in their carotid artery, might be susceptible to severe injury through day-to-day activity. A sufficient force placed on the patient's neck could cause the stent to collapse, resulting in injury to the patient. In order to prevent this, self-expanding stents have been proposed for use in such vessels. Self-expanding stents act like springs and will recover to their expanded or implanted configuration after being crushed.

One type of self-expanding stent is disclosed in U.S. Pat. No. 4,655,771, which stent has a radially and axially flexible, elastic tubular body with a predetermined diameter that is variable under axial movement of the ends of the body relative to each other and which is composed of a plurality of individually rigid but flexible and elastic thread elements defining a radially self-expanding helix. This type of stent is known in the art as a "braided stent" and is so designated herein. Placement of such stents in a body vessel can be achieved by a device that comprises an outer catheter for holding the stent at its distal end, and an inner piston that pushes the stent forward once it is in position.

However, braided stents have many disadvantages. They typically do not have the necessary radial strength to effectively hold open a diseased vessel. In addition, the plurality of wires or fibers used to make such stents could become dangerous if separated from the body of the stent, where they could pierce through the vessel. Therefore, there has been a desire to have a self-expanding stent that is cut from a tube of metal, which is the common manufacturing method for many commercially available balloon-expandable stents. In order to manufacture a self-expanding stent cut from a tube, the alloy used would preferably exhibit superelastic or pseudoelastic characteristics at body temperature, so that it is crush recoverable.

The prior art makes reference to the use of alloys such as Nitinol (Ni—Ti alloy), which have shape memory and/or superelastic characteristics, in medical devices that are designed to be inserted into a patient's body. The shape memory characteristics allow the devices to be deformed to facilitate their insertion into a body lumen or cavity and then be heated within the body so that the device returns to its original shape. Superelastic characteristics, on the other hand, generally allow the metal to be deformed and restrained in the deformed condition to facilitate the insertion of the medical device containing the metal into a patient's body, with such deformation causing the phase transformation. Once within the body lumen, the restraint on the superelastic member can be removed, thereby reducing the stress therein so that the superelastic member can return to its original un-deformed shape by the transformation back to the original phase.

Alloys having shape memory/superelastic characteristics generally have at least two phases. These phases are a martensite phase, which has a relatively low tensile strength and which is stable at relatively low temperatures, and an austenite phase, which has a relatively high tensile strength and which is stable at temperatures higher than the martensite phase.

Shape memory characteristics are imparted to the alloy by heating the metal at a temperature above which the transformation from the martensite phase to the austenite phase is complete, i.e. a temperature above which the austenite phase is stable (the $A_f$ temperature). The shape of the metal during this heat treatment is the shape "remembered." The heat-treated metal is cooled to a temperature at which the martensite phase is stable, causing the austenite phase to transform to the martensite phase. The metal in the martensite phase is then plastically deformed, e.g. to facilitate the entry thereof into a patient's body. Subsequent heating of the deformed martensite phase to a temperature above the martensite to austenite transformation temperature causes the deformed martensite phase to transform to the austenite phase, and during this phase transformation the metal reverts back to its original shape if unrestrained. If restrained, the metal will remain martensitic until the restraint is removed.

Methods of using the shape memory characteristics of these alloys in medical devices intended to be placed within a patient's body present operational difficulties. For example, with shape memory alloys having a stable martensite temperature below body temperature, it is frequently difficult to maintain the temperature of the medical device containing such an alloy sufficiently below body temperature to prevent the transformation of the martensite phase to the austenite phase when the device was being inserted into a patient's body. With intravascular devices formed of shape memory alloys having martensite-to-austenite transformation temperatures well above body temperature, the devices can be introduced into a patient's body with little or no problem, but they must be heated to the martensite-to-austenite transformation temperature, which is frequently high enough to cause tissue damage.

When stress is applied to a specimen of a metal such as Nitinol exhibiting superelastic characteristics at a temperature above which the austenite is stable (i.e. the temperature at which the transformation of martensite phase to the austenite phase is complete), the specimen deforms elastically until it reaches a particular stress level where the alloy then undergoes a stress-induced phase transformation from the austenite phase to the martensite phase. As the phase transformation proceeds, the alloy undergoes significant increases in strain but with little or no corresponding increases in stress. The strain increases while the stress remains essentially constant until the transformation of the austenite phase to the martensite phase is complete. Thereafter, further increases in stress are necessary to cause further deformation. The martensitic metal first deforms elastically upon the application of additional stress and then plastically with permanent residual deformation.

If the load on the specimen is removed before any permanent deformation has occurred, the martensitic specimen will elastically recover and transform back to the austenite phase. The reduction in stress first causes a decrease in strain. As stress reduction reaches the level at which the martensite phase transforms back into the austenite phase, the stress level in the specimen will remain essentially constant (but substantially less than the constant stress level at which the austenite transforms to the martensite) until the transformation back to the austenite phase is complete, i.e. there is significant recovery in strain with only negligible corresponding stress reduction. After the transformation back to austenite is complete, further stress reduction results in elastic strain reduction. This ability to incur significant strain at relatively constant stress upon the application of a load, and to recover from the deformation upon the removal of the load, is commonly referred to as superelasticity or pseudoelasticity. It is this property of the material which makes it useful in manufacturing tube cut self-expanding stents.

The prior art makes reference to the use of metal alloys having superelastic characteristics in medical devices that are intended to be inserted or otherwise used within a patient's body. See for example, U.S. Pat. No. 4,665,906 (Jervis) and U.S. Pat. No. 4,925,445 (Sakamoto et al.). However, the prior art has yet to disclose any suitable tube-cut self-expanding stents. In addition, many of the prior art stents lacked the necessary rigidity or hoop strength to keep the body vessel open. In addition, many of the prior art stents have large openings at their expanded diameter. The smaller the openings are on an expanded stent, the more plaque or other deposits it can trap between the stent and the vessel wall. Trapping these deposits is important to the continuing health of the patient in that it helps prevent plaque prolapse into the vessel, restenosis of the vessel it is implanted into, and strokes caused by the release of embolic particles into the bloodstream.

One additional concern with stents, and with other medical devices, is that they may exhibit reduced radiopacity under X-ray fluoroscopy. To overcome this problem, it is common practice to attach markers made from highly radiopaque materials to the stent, or to use radiopaque materials in plating or coating processes. Those materials are typically gold, platinum, or tantalum. The prior art makes reference to these markers or processes in U.S. Pat. No. 5,632,771 (Boatman et al), U.S. Pat. No. 6,022,374 (Imran), U.S. Pat. No. 5,741,327 (Frantzen), U.S. Pat. No. 5,725,572 (Lam et al), and U.S. Pat. No. 5,800,526 (Anderson et al). However, due to the relative position of these materials in the galvanic series versus the position of the base metal of the stent in the galvanic series, there is a certain challenge to overcome; namely, that of galvanic corrosion.

In addition, biodegradable stents and stents fabricated from polymeric materials that avoid the use of metallic materials must still be able to be visualized under X-ray fluoroscopy. For these types of devices a major challenge exists in how to impart/increase the radiopacity of these devices with out the use of radiopaque markers or coatings. The prior art makes reference to one such method in U.S. Pat. No. 4,935,019 (Papp), in which a radiopaque, polymeric composition suitable for printing onto surgical fabrics provides an X-ray detectable marker, said marker is obtained by dispersing a heavy metal salt such as barium sulfate in a liquid polymer carrier. In Papp, the barium sulfate has an average particle size greater than about 5 microns and is present in an amount of from about 15 to 90% by weight of total solids of said composition. Papp indicates that barium sulfate comprising from about 60 to 90% by weight of solids of said composition is preferred. However addition of barium sulfate in large percentage quantities such as this may affect the integrity of the base material, reducing strength, and adversely affecting other mechanical properties and characteristics. In biodegradable polymers, the impact of radiopaque additives may also affect properties such as degradation rates of bioabsorbable polymers, elasticity, while potentially adding the presence of stress risers in and around any localized concentration of barium sulfate particles within the material. Furthermore, inorganic contrast agents such as barium sulfate and zirconium oxide do not readily dissolve or do not easily disperse in organic solvents, which are commonly used to dissolve nondegradable and biodegradable polymers.

Accordingly, there is a need for a radiopaque material or agent that can be easily added to biostable polymeric and biodegradable polymeric materials which readily dissolves into the polymer so that the resulting composite material is adequately radiopaque and which will not adversely affect the material or mechanical properties of the material one desires to make radiopaque.

BRIEF SUMMARY OF THE INVENTION

The high intensity X-ray contrast agent in accordance with the present invention overcomes the disadvantages and shortcomings of what is currently available and satisfies the unmet needs of imaging medical devices, particularly non-metallic medical devices by maximizing the intensity of the x-ray contrast agent both through primary and secondary effects. Primary effects include incorporating the radiopaque element and maximizing the content of this element in the contrast agent through chemistry, while secondary effects include optimizing the location of the radiopaque element within the polymer. Essentially by selectively maximizing and incorporating the iodine content within and dispersed throughout the polymer one can tune the radiopacity of polymeric materials to levels previously not available. Moreover, the creation and optimization of this contrast agent allows for improved processing characteristics when combined with polymeric materials and as such may further reduce manufacturing costs while providing a polymeric material with improved high intensity radiopacity with a satisfactory degradation profile.

The present invention relates to a high intensity dendritic or star-shaped contrast agent suitable for use with implantable polymeric medical devices or for a polymeric coating of an implantable medical device. Multivalent hydroxyl or amine containing organic compounds such as pentaerythritol, bis-pentaerythritol glycerol, polyhydric mono- and di-saccharides, etc., can be used to react with an iodine containing aromatic compounds such as 2,3,5-triiodobenzoic acid to form such high iodine containing compounds. Each such compound may contain a multiple of three (3) iodine atoms, greatly intensifying the x-ray image of a medical device fabricated from a material containing such a compound. The iodine content in such a high intensity dendritic contrast agent may be as high as 85% using commercially available dendritic polyamine precursors.

In an exemplary embodiment of the present invention, the contrast agent may contain a multiplicity of iodine atoms or bromine atoms or a combination of both in a single molecule in order to enhance the x-ray image produced by dispersing the agent throughout the material that either the device will be fabricated from or applied as a coating to the device. In accordance with the present invention, the contrast agent can be constructed from any core of dendrimer containing free functional groups such as amine, hydroxyl, sulfhydryl, isocyanate, and result in a molecule containing a multiple of three (3) iodine or bromine or a combination of both atoms with each additional conjugation of small iodine or bromine containing building block, such as triiodobenzoic acid or as triiodobenzoic acid chloride. When constructed in this fashion, the contrast agent may be substantially soluble in common organic solvent such as acetone, dimethylacetamide (DMA), dimethylsulfoxide (DMSO), acetone, THF, 1,4-dioxane, DCM etc. and also has substantially good miscibility with common organic polymers such as PLGA, PLA etc. The contrast agent in accordance with the present invention can form a solid solution with a polymer matrix that can then form the basis of a medical device. The contrast agent in accordance with the present invention is substantially biocompatible and can be added to polymer or polymer mixtures, and/or inorganic/organic composite materials to enhance its X-ray image quality.

In another exemplary embodiment of the present invention, the contrast agent may be mixed with the bulk material by various means such as solvent casting, injection and/or compression molding in order to form a medical device or a coating for a medical device. The bulk form can then be processed to final size and shape by traditional fabrication methods. Alternatively, the polymeric coating with the contrast agent included can be applied to the surface of an implantable medical device employing traditional coating methods In yet another exemplary embodiment of the present invention, selective incorporation of the contrast agent to a polymeric structure can be accomplished in a number of ways. By ensuring placement of the contrast agent in certain areas of the polymer structure and not in other areas, additional secondary improvements in radiopacity can be realized without affecting material and/or mechanical properties. One such example is incorporation of the contrast agent at the proximal and distal ends of the polymer chain. By utilizing methods such as orientrusion, which may provide for a high degree of molecular orientation of the polymer chains within the polymer, one can create a polymeric material with high intensity radiopacity at the select portions of the bulk material which would be significantly more radiopaque than the surrounding areas where the contrast agent was not present. Likewise the selective placement of the contrast agents in the coating material can provide one with secondary benefits similar to those obtained with selective placement of the contrast agents in the bulk material.

In yet another exemplary embodiment of the present invention, selective incorporation of the contrast agent to a polymeric structure can be accomplished through a covalent conjugation process at either of the distal and proximal end, or both ends of a biostable and/or biodegradable polymer chain. Such polymers with inherent radiopacity can be used to either build implantable devices or as a coating for an implantable medical device.

Furthermore the incorporation or application of biological and/or pharmaceutical agents with or onto the material can provide additional benefits when used in combination with the present invention, and as such is a further object of this invention. Compounds such as those identified below may be applied as coatings on these devices or incorporated within the polymer and may be used to deliver therapeutic and pharmaceutical agents which may include: anti-proliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); anti-platelet agents such as G(GP) $11_b/111_a$ inhibitors and vitronectin receptor antagonists; anti-proliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC); anti-proliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetaminophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blockers; nitric oxide donors; antisense oligonucleotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); and protease inhibitors.

The use of compounds in conjunction with the present invention can provide distinct clinical advantages over existing therapies and/or devices. More specifically, compounds that are capable of causing lysis or degradation of the embolic debris can be incorporated into the filtering portion of the present invention. A factor to consider in the selection of such a compound is the origin of the debris be it thrombus, plaque, atheroma, or any other form representing an embolus. As the mesh and or pore size of the filtering aspect of the present invention decreases, more embolic material may become trapped in the filtering mechanism of the present invention, thereby increasing the load on the filtering portion. While small emboli (typically smaller than 100 microns) are not a major concern because of the body's natural ability to enzymatically degrade, digest or lyse the emboli, the embolic load on the filter itself can be overloaded and result in formation of a thrombus if the blood flow is significantly slowed to the point which allows for a thrombus formation. In this situation the incorporation or application of compounds, which can degrade trapped emboli, can be beneficial. Some exemplary suitable compounds may include: Tissue Plasminogen activator (TPA); Streptokinase (SK); Reteplase; Tenecteplase; Urokinase; Lanoteplase; Staphylokinase; and/or Nadroparin (anti-factor Xa). In addition, the filtering portion of the present invention may incorporate an antithrombotic and/or antithrombogenic agent to prevent the formation of a thrombus. Some exemplary compounds may include: Heparin; Fragmin (dalteparin, low MW Heparin); a monoclonal antibody such as ReoPro™ (abciximab, antiplatelet antibodies) Acenocoumarol; Anisindione; Dicumarol; Warfarin; Enoxaparin (Lovenox); Anagrelide (Agrylin); Indomethacin (Indocin); Dipyridamole; Clopidogrel; Aggrenox; and/or Coumadin. Furthermore, an affinity-binding compound may also be incorporated with the filtering aspect of the present invention by itself or in combination with other compounds. Affinity-binding compounds can promote the binding and/or adhesion of embolic material thus facilitating entrapment of embolic material and subsequent removal from the blood stream. Whether incorporated into the strut or membrane by methods such as chemical surface treatments, bombardment, placement into reservoirs, or in the case of polymeric struts and membranes, blended with the material itself, or by application of a coating to the struts and/or membranes with a compound, any identified compound or combination of identified compounds may be used. Furthermore any number of compounds may suggest themselves to one who is skilled in the art and may be utilized in connection with the present invention alone or in combination with other compounds.

The foregoing exemplary embodiments of the present invention provide a high intensity radiopaque contrast agent which may be used independently, for example as a coating or may be incorporated within a polymeric material to be subsequently fabricated into medical devices in accordance with the present invention. Moreover, the incorporation of drugs and/or agents may be combined with the high intensity contrast agent to realize additional synergistic benefits. As noted above, the incorporation of biological and/or pharmaceutically active agents with the present invention can be utilized for the additional purposes of preventing thrombus formation, promotion of binding, and degradation of thrombus, all of which provide a patient benefit.

BRIEF DESCRIPTION OF THE DRAWINGS

Aspects of the present invention as well as the preceding information may best be understood with reference to the subsequent detailed description taken in conjunction with the accompanying exemplary drawings in which:

FIGS. 2A and 2B show the coupling reaction between any of the polyamine dendrimers with 2,3,5-triiodobenzoic acid chloride to yield corresponding dendritic iodine-containing contrast agent (A); and a schematic drawing of a dendritic polyamine up to level 4 (B) as used in the present invention.

FIG. 3 shows the chemical structure of a level 1 polyamine dendritic derived high intensity iodine containing contrast agent.

FIG. 4 shows the chemical structure of a level 2 polyamine dendritic derived high intensity iodine containing contrast agent.

FIG. 5 shows the chemical structure of a level 3 polyamine dendritic derived high intensity iodine containing contrast agent.

FIG. 6 shows the chemical structure of a level 4 polyamine dendritic derived high intensity iodine containing contrast agent.

FIGS. 12A and 12B show schematically the random orientation of polymer strands/chains in a matrix (12A) and the aligned orientation of polymer strands/chains in a polymer that has undergone orientrusion (12B).

DETAILED DESCRIPTION OF THE PREFERRED EMBODIMENTS

Figure 1:
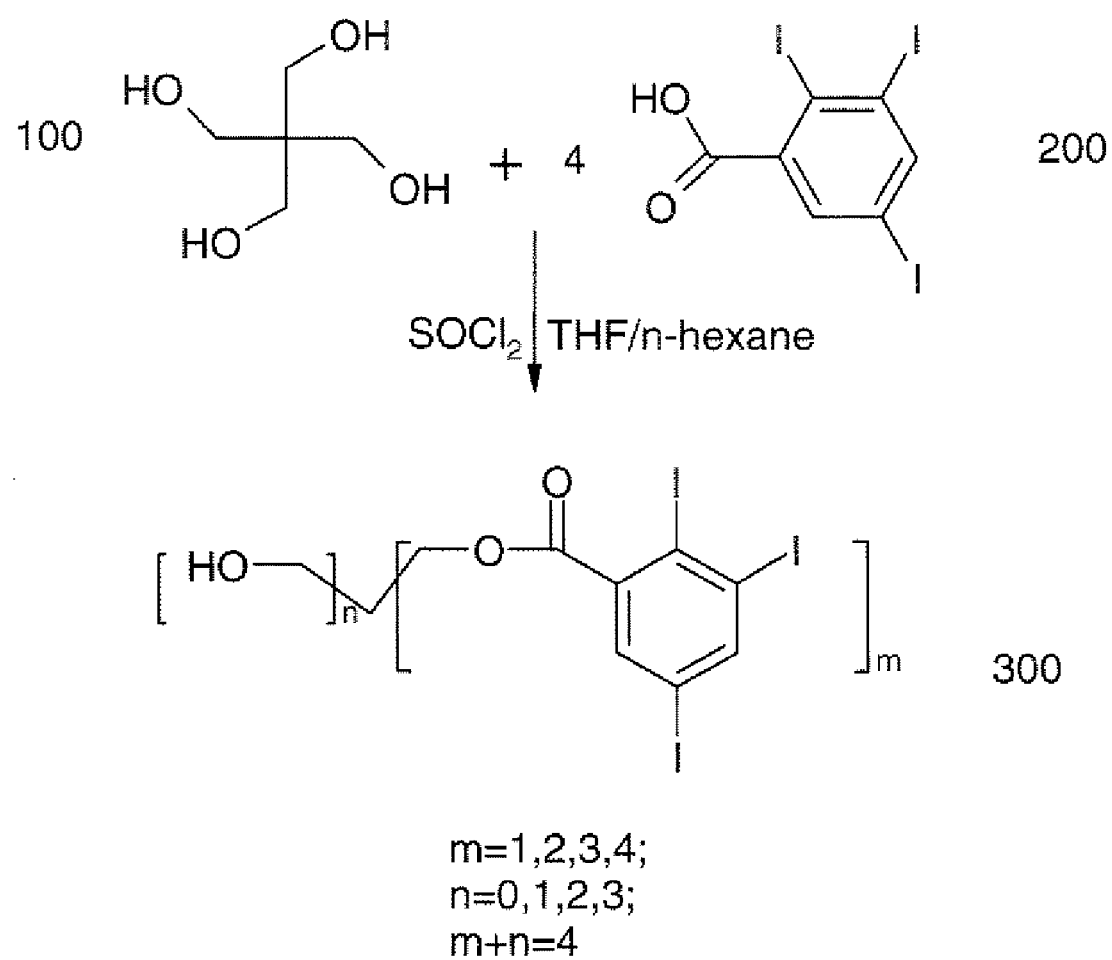
FIG. 1 shows the coupling reaction between pentaerythritol and 2,3,5-triiodobenzoic acid and the reaction products wherein, $SOCl_2$ is the catalyst or activating agent, and THF/Hexane is the reaction medium or solvent for the reaction. The end product is a star-shaped high-density contrast agent.
Figure 7:
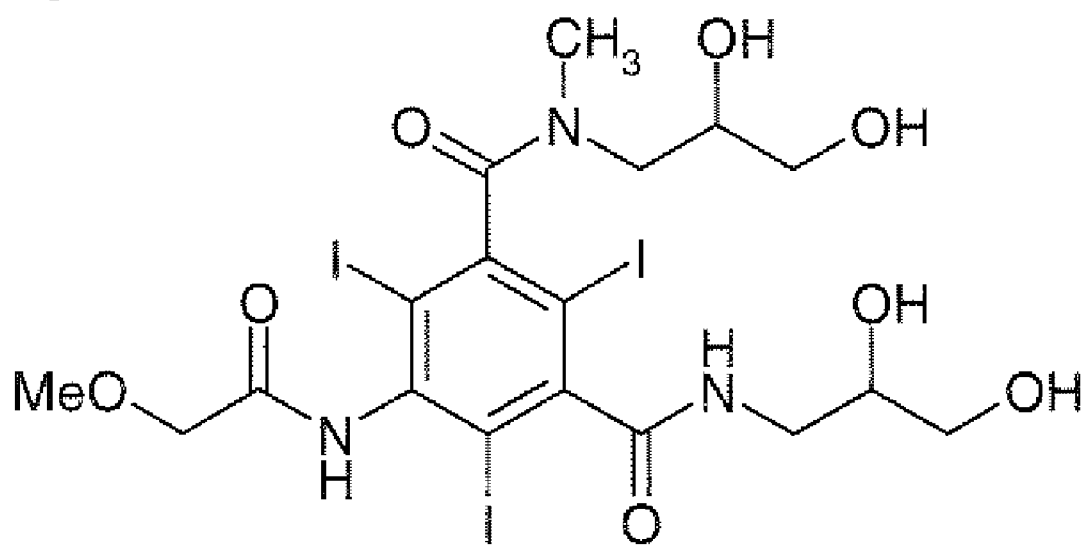
FIG. 7 shows the chemical structure of a commercially available water soluble contrast agent known in the art under the trade name Ultravist®.

As shown in FIG. 1, when reacting pentaerythritol (100) with 2,3,5-triiodobenzoic acid (200) in the presence of $SOCl_2$ (the catalyst) and THF/Hexane (the reaction medium), the resulting contrast agent (300) may have a high iodine content of 85%, almost twice as high as commercially available agents (50) such as those under the trade name Ultravist® as shown in FIG. 7. In the reaction scheme, the number of benzoic acid moiety is denoted by m which is an integer between 1 and 4, depending on the completeness of the reaction. The number of unreacted hydroxyl group in the final compound is denoted by n, which is an integer between 0 and 3, depending again on the completeness of the reaction. The sum of m and n, however, should always be 4 which corresponds to the number of hydroxyl groups in the starting pentaerythritol. FIG. 2A shows an exemplary coupling reaction between a polyamine-terminated dendrimer with 2,3,5-triiodobenzoic acid chloride to yield a corresponding dendritic iodine containing contrast agents. In the reaction scheme, R' denotes the portion of a dendrimer without the $(NHR)_n$ portion as depicted in FIG. 3 (level 1 dendrimer in which n=2), in FIG. 4 (level 2 dendrimer in which n=4), in FIG. 5 (level 3 dendrimer in which n=8), and in FIG. 6 (level 4 dendrimer in which n=16). In the reaction scheme, n is the total number of amine groups in a starting dendrimer that can be utilized in the coupling reaction. The total number of iodine atoms in each is 3n since each amine group after the reaction will yield 3 iodine atoms on the benzene ring. For example, for level 1 dendrimer in FIG. 3, there are 2 amine groups in the starting dendrimer. The final iodine atom is 3×2=6 after the conjugation reaction. Likewise, FIG. 4 shows the conjugation reaction of a level 2 dendrimer and final dendritic contrast agent with 12 iodine atoms. FIG. 5 shows a level 3 dendritic contrasting agent with 24 iodine atoms. FIG. 6 shows a level 4 dendritic contrasting agent with 48 iodine atoms. FIG. 2b shows a generic chemical structure of a dendritic compound used in the present invention with various levels denoted therein. Similarly dendrimers containing other functional groups such as carboxyl, hydroxyl, and sulfhydryl groups can also be used as the building blocks of high intensity contrast agents in accordance with this invention. As shown for the chemical structure of a commercially available contrast agent (50), known under the trade name Ultravist® in FIG. 7, each such molecule only contains 3 iodine atoms covalently linked to the core benzene ring. The I—C bonds are demonstrated to be stable under physiological and irradiation conditions. The compound is mainly eliminated through renal dialysis.

Figure 8:
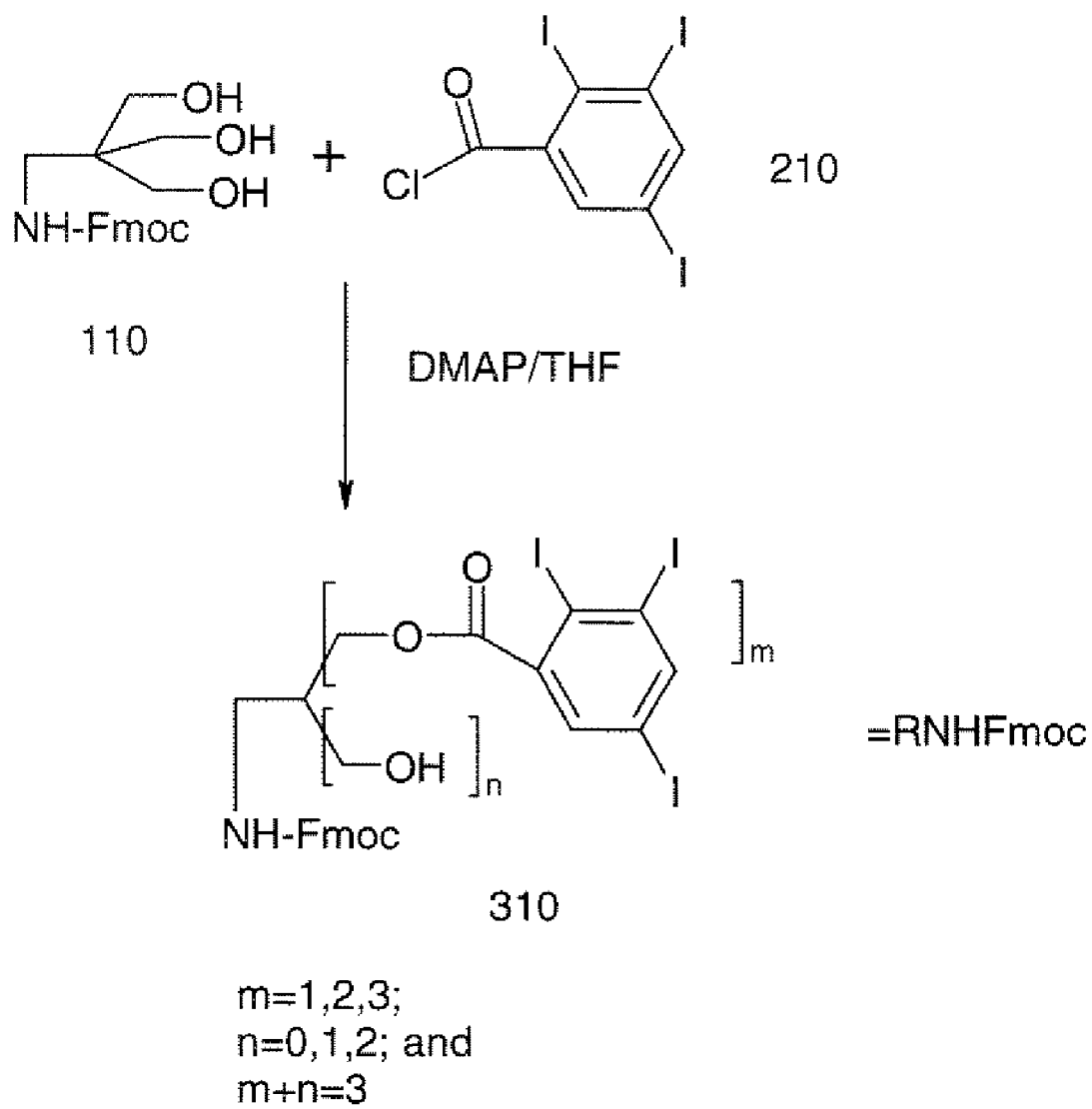
FIG. 8 shows the reaction of an Fmoc-protected polyhydroxyl compound with 2,3,5-triiodobenzoic acid chloride to yield a protected high density iodine-containing initiator.

The Iopromide compound in Ultravist® has multiple hydroxyl groups that make it soluble in water. Although the water solubility of this agent makes it suitable for use as an injectable contrast agent, it may not perform as well when used as a radiopaque coating or as a radiopaque additive in a polymer matrix. Such increase of side group makes the weight percentage of iodine in the molecule relatively low. In contrast, in accordance with the present invention, the linking of a multiple triiodobenzene ring structure to a core dendritic structure so the iodine content in each molecule is maximized can create a high intensity contrast agent suitable as an radiopaque additive as both a coating and an additive to a polymer matrix as well as other uses known to those skilled in the art. As shown in FIG. 8, the simplest form of such a high iodine content contrast agent is synthesized through the reaction between a 9-fluorenylmethyl (Fmoc)-protected 1-amino-2,2-dihydroxymethyl-3-propanol (110) and three 2,3,5-triiodobenzoic acid chloride (210). In FIG. 8, m denotes the number of the triiodobenzene moiety in the final contrast agent and is an integer between 1 and 3. N is the unreacted hydroxymethyl group in the final compound and is an integer between 0 and 2. The sum of m and n equals 3. When the reaction proceeds to completion, the resulting contrast agent (310) has an iodine content of about 74%, much higher than Ultravist's 48% (50). Additional advantages of a contrast agent in accordance with the present invention are that all raw materials are readily available and the coupling reactions generally have a high yield. Multiple layers of dendrimer cores may increase the cost, but this may be offset by ever-higher iodine content and reduced amount of the required agent in the medical device to achieve adequate image contrast. Increased molecule weight also reduces the mobility and potential of the contrast agent to leach out of the medical device.

Reacting a hydroxyl- or an amine-group containing compound and an iodine containing aromatic carboxylic acid or carboxylic acid chloride compound with a catalyst may be used to synthesize an iodine containing contrast agent. In accordance with the present invention this reaction is expanded further by using a bi-, tri- or tetra-hydroxyl containing compounds such as ethylene glycol, propylene glycol, glycerol, and pentaerythritol, bis-pentaerythritol to a single reactive contrast agent with a multiple number of iodine atoms, which may result in maximizing the radio-opacity of the molecule.

In-house research has showed that commercially available injectable contrast agents such as those under the trade name Ultravist® (50) (Ultravist is a Registered Trademark of Schering AG) (iopromide containing 3 iodine atoms in each Ultravist molecule) demonstrated comparable x-ray contrast to barium sulfate. The contrast agents in accordance with the present invention have up to two times (2×) more iodine atoms per unit weight of contrast agent, which may provide up to an estimated four times (4×) sharper contrast image quality. In addition, the proposed contrast agent is sparingly water-soluble and would not swell the polymer matrix of the medical device and thus better maintain the mechanical properties of a medical device. In addition to limiting the swelling, the leaching of the agent is also minimized.

In accordance with the present invention, multiple iodine molecules are built into a single contrast agent resulting in maximizing the radio-opacity of the contrast agent. Moreover, because good solubility of the contrast agent is present in common organic solvents, good miscibility may result with common polymers or polymer blends to form solid solutions. Enhanced mechanical strength of the bulk materials is maintained due to the elimination of crystalline additives which may result in stress risers, while relatively low water solubility ensures long residence time and degradation rate of the bulk material.

Additional modifications in accordance with the present invention such as use of various hydroxyl or amine containing functional molecules in the reaction may be beneficial. Typical examples include, ethylene glycol, propylene glycol, glycerol, pentaerythritol. Other functional group containing compounds such as carboxyl groups, may be used for the synthesis of the high intensity contrast agent compounds and naturally derived amine or polyhydric alcohols such as sorbitol, trehelose etc. may be used to construct such a contrast agent and in addition may provide good biocompatibility. As previously indicated, various processing methods such as solvent casting, dip coating, injection molding etc. may be used to mix the contrast agent and a bulk material.

Figure 9:
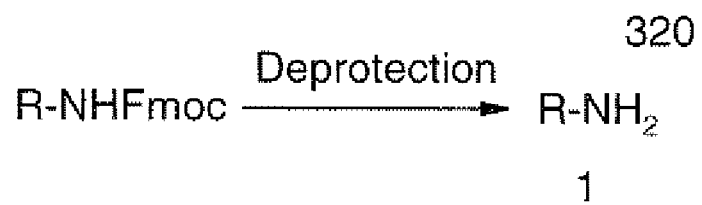
FIG. 9 shows the deprotection reaction of compound in FIG. 8 to yield the high density iodine containing amine initiator.
Figure 10:
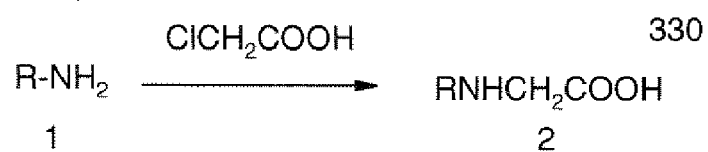
FIG. 10 shows transformation of amine-terminated initiator to a carboxyl-ended contrast agent.
Figure 11:
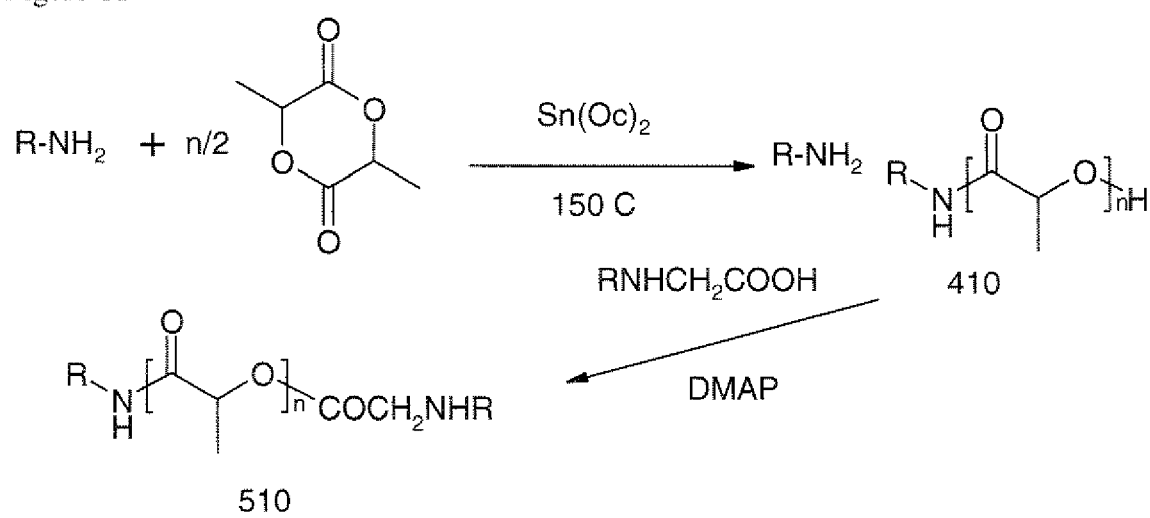
FIG. 11 shows the reaction between the compound synthesized in FIG. 9 and lactide to yield a bioabsorbable polymer terminated with high density iodine contrast agent on one end (step 1); coupling reaction between carboxyl terminated initiator synthesized in FIG. 10 to yield a bioabsorbable polylactide (PLA) terminated with high density iodine contrast agent on both ends (step 2).

In accordance with the present invention, compositions of a new class of polymeric high intensity x-ray contrast agents suitable for imaging implanted medical devices such as a drug eluting stent are formulated. Protected polyhydric alcohol or amine containing organic compounds commonly used in the synthesis of dendrimers may be used to react with an iodine containing aromatic compounds such as 2,3,5-triiodobenzoic acid to form such high iodine containing initiators. Each such initiator may contain a multiple of three (3) iodine atoms. Upon deprotection of Fmoc group, as shown in FIG. 9, these iodine rich compounds possess a free amine group and can serve as an initiator for a ring opening reaction (ROP) of cyclic lactones such as lactide, glycolide etc. to form a bioabsorbable polymers. Other functional dimers such as a dilactams, lactone such as caprolactone, mixed dilactones, mixed cyclophosphoester, trimethylene carbonate (TMC), may also be used in the reaction. Optionally as shown in FIG. 10, the amine end-capped initiator can be transformed to a carboxyl end-capped high iodine functional moiety by chloroacetic acid and later on used to cap the remaining end of a bioabsorbable polymer initiated with a iodine compound made in FIG. 9. As shown in FIG. 11, the initiator created in FIG. 9 is then used to initiate a cyclic dimmer through ROP to form a bioabsorbable polymer with high iodine content on one end (410). The resulting polymer can be further conjugated to a iodine containing compound created in FIG. 10 to yield a bioabsorbable polymer that have iodine atoms on both ends (510). This additional iodine containing moiety at the end of the polymer doubles the iodine content in the final bioabsorbable polymer and further enhances the x-ray image contrast. Similarly di-functional iodine rich compounds can be used in building other types of polymers such as polyurethanes and polyureas. The specific advantages of such a compound include but are not limited to: iodine containing bioabsorbable polymers which behave like bioabsorbable polymers used to make the matrices of a medical device such as a drug eluting stent; these compounds are soluble in common organic solvents; the molecular weight and other properties of such iodine containing bioabsorbable polymers can be adjusted to vary the degradation time, mechanical strength, and contrast intensity per polymer; the iodine-containing polymers in accordance with the present invention are miscible with the bulk materials used to construct a medical device, avoiding the change of degradation time and mechanical strength, and are not water-soluble and do not leach out during the manufacturing processes and initial implantation period.

FIGS. 12A and 12B show the orientation of polymer strands in a polymer matrix. Although the normal orientation of polymer chains in a polymer matrix (10) is random, one can impart a forces and/or processing conditions to create an alignment of the polymer chains within the structure (11) that may result in anisotropic material properties and may lead to improved material and/or mechanical properties. In accordance with the present invention, the polymers having high intensity contrast properties can be similarly processed to achieve the desired mechanical properties.

Figure 13:
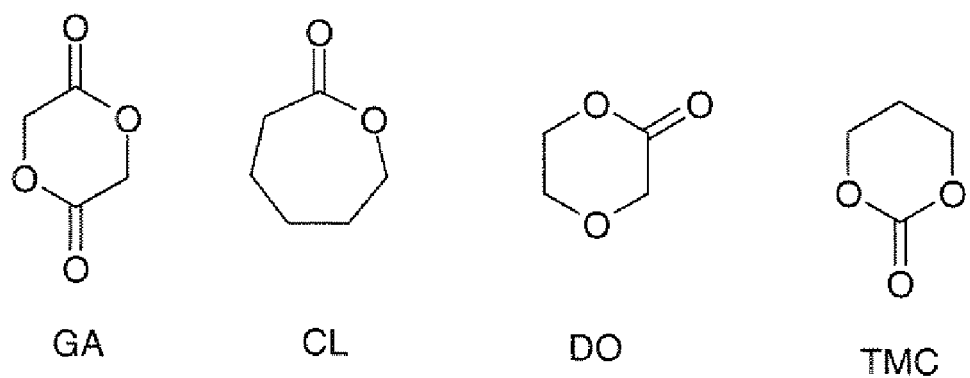
FIG. 13 shows the chemical structure of exemplary dimers (glycolide, caprolactone, p-dioxanone, and trimethylene carbonate) used for making bioabsorbable polymers and/or copolymers.
Figure 14:
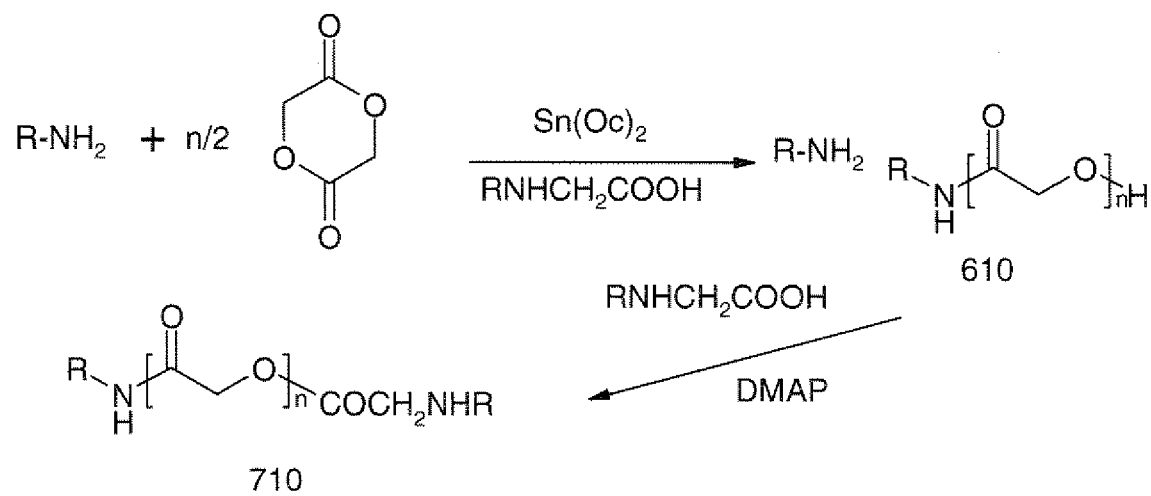
FIG. 14 shows the reaction between the compound synthesized in FIG. 9 and glycolide (GA) to yield a bioabsorbable polyglycolide (PGA) terminated with high density iodine contrast agent on one end (step 1); coupling reaction between PGA synthesized in step 1 and carboxyl terminated radiopaque compound synthesized in FIG. 10 to yield a bioabsorbable polyglycolide (PGA) terminated with high density iodine contrast agents on both terminals (step 2).

Similarly, other commonly used cyclic dimers as shown in FIG. 13, for ring opening reactions such as glycolide (GA), caprolactone (CL), p-Dioxanone (DO), trimethylene carbonate (TMC) can all be used in the polymerizations alone or in mixture. Such dimers alone such as in FIG. 14 showing an ring opening reaction of glycolide (GA) to yield a bioabsorbable polyglycolide (PGA, 610), and end capping reaction with an iodine containing functional moiety to yield PGA (710) with 2× radiopaque density of 610. These cyclic dimmers may be used in combination with each other to adjust the physical and chemical properties of the final copolymers. These combinations are known to the skilled in the arts.

Additional embodiments and/or modifications include a series of functional iodine or bromine containing initiators used to initiate the ring opening reactions of a bioabsorbable polymer such as lactide, glycolide, caprolactone, or the mixture therein. Difunctional iodine or bromine rich compounds may serve as a building block of non-degradable polymers such as polyurethanes and polyureas. These polymeric structures can be further modified by having a biodegradable and/or biostable polymer containing multiple iodine atoms at one end or both ends of the polymer chains. This is accomplished by utilizing a process in accordance with the present invention for end capping an iodine or bromine containing biodegradable and/or biostable polymer at the end of the reaction to double the iodine atoms in the polymer chain. Moreover this process in accordance with the present invention may be used to form X-ray visible bulk material of a medical device using such iodine or bromine containing bioabsorbable polymers providing the necessary radiopacity. Alternately this process, in accordance with the present invention, for adding such iodine or bromine containing bioabsorbable polymers may be used to enhance the X-ray contrast intensity of the bulk of the medical device. Furthermore one is not limited to bioabsorbable polymers as this process, in accordance with the present invention, for using such iodine or bromine containing non-degradable or biostable polymers may be utilized to form X-ray visible bulk material of a medical device. The process in accordance with the present invention may also enhance the X-ray contrast intensity of the bulk of the medical device by adding such iodine or bromine containing nondegradable or biostable polymers to the bulk of the medical device.

A simple calculation of iodine content may show that with an iodine rich compound one has an iodine content of 72.7%. When incorporated into the final polymer with a degree of polymerization (DP) of 200 (molecular weight is ca. 30 KD), the iodine content in the final polymer is approximately 3.81%, which is adequate for visibility under normal x-ray operating conditions. If the final end-capping step in accordance with the present invention is used, the iodine content in the final polymer may be doubled to 7.25%, achieving a value much higher than 3.0% to 5.0% iodine content needed for acceptable x-ray opacity. Alternatively, the Molecular weight of the polymer may be doubled to around 60 Kilo Daltons (KD) without adversely affecting the radiopacity since the polymer would still have adequate X-ray opacity with the end-capping process of the present invention.

The method for introducing iodine or bromine atoms into each repeating monomer as disclosed in U.S. Pat. No. 6,475, 477, (which is hereby incorporated by reference) may cause the property of bulk polymer to change as a result of iodine or bromine introduction which is distributed throughout the polymeric material. This series of patents were also limited to iodine or bromine containing polycarbonates. In comparison, the current method in accordance with the present invention clusters iodine atoms and/or selectively locates the atoms at one end or both ends of a polymer chain, leaving the bulk of the polymer chains intact for its role as a medical device and thereby not producing a change in the properties of the bulk material which may affect device performance.

This disclosed invention applies to both degradable and bioabsorbable polymer synthesis as well as non-degradable/biostable polymers. The incorporation of the high density radiopaque contrast agents can be added to a biostable polymer through grafting polymerization or plasma grafting processes. The x-ray opaque polymers may be further processed into different forms and shapes as medical devices providing the bulk material from which the end product or device is formed. The polymers may also be used as a polymeric coating or a drug release barrier for device drug combination products or to simply enhance the radiopacity of the device for which the material is coated upon or incorporated within.

The reaction between a hydroxyl group containing compound and an iodine containing aromatic compound may be processed for synthesizing an iodine containing contrast agent. This invention expands the concept further and used a protected bi-, tri- or tetra-hydroxyl containing compounds to make a functional initiator. Upon deprotection of Fmoc (9-fluorenylmethoxycarbonyl) as shown in FIG. 9, the initiator can be used to initiate a ring opening reaction of cyclic lactones such as lactide, glycolide to form an iodine-containing polymer. Other commonly used protecting groups for amine and hydroxyl groups, other than Fmoc, such as Boc-, Z-, Ddz-, tert.-Butyl, Cbz, may be expressly used to substitute for Fmoc as a suitable protecting group in the reaction. The ring opening reaction is well researched and used in production of other biocompatible materials such as resorbable sutures. The final end-capping step as shown in FIGS. 11 and 13 is a variation of regular end capping of a methanol, to impart more iodine content of the bioabsorbable polymer.

In accordance with the present invention, multiple iodine molecules are built into a single initiator of a ring opening reaction. A bioabsorbable polymer contains a large number of iodine atoms without sacrificing the mechanical properties of the bulk materials, for example, such a bioabsorbable polymer may contain twice the number of iodine atoms by end capping with a derivative of the iodine containing functional initiator. Such iodine containing bioabsorbable polymer can be blended with regular bulk materials to form a medical device with much enhanced x-ray contrast and is non-leachable during the processing and initial period of implantation, ensuring desired degradation and biocompatibility. Furthermore, the contrast intensity of the medical device can be adjusted by varying the molecular weight and the percentage of the iodine-containing polymer in the matrices. This iodine introduction method may be used for synthesis of radiopaque non-degradable polymer as well in accordance with the present invention.

Modifications include use of various hydroxyl or amine containing functional molecules, which upon proper protection, can be used in the synthesis of the functional initiator. Upon deprotection, these functional initiators can be transformed into corresponding end capping iodine containing functional compounds. Any commonly monomers for bioabsorbable polymers such as lactide, glycolide, caprolactone, dioxanone, trimethylene carbonate, etc., or the combination of these monomers, can be used to construct the iodine-containing degradable polymers. Non-degradable polymers such as polyurethanes or polyureas may also be made more radiopaque using the same or similar chemistry.

Although what has been shown and described is what is believed to be the most practical and preferred embodiment of the present invention, other forms of, and departures from the specific designs described and shown, will suggest themselves to those skilled in the art and may be used without departing from the spirit, scope or essential characteristics of the present invention. The present invention is not restricted or limited to the foregoing described embodiments, but rather should be constructed to cohere with all variations, combinations, and modifications that may fall within the scope of the appended claims.

What is claimed is:

1. A compound having the following formula:

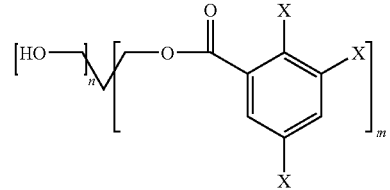

wherein m is an integer between 1 and 4, n is an integer between 0 and 3, and m+n=4, and wherein X is a halogen atom selected from the group consisting of Chlorine, Bromine, and Iodine.

2. A radiopaque material comprising the compound of claim 1.

3. A compound having the following formula:

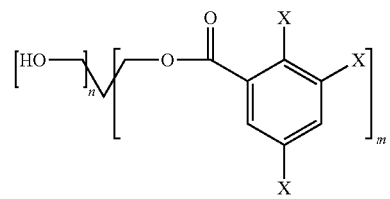

where m=4 and n=0, and X is Iodine.

4. A compound having the following formula:

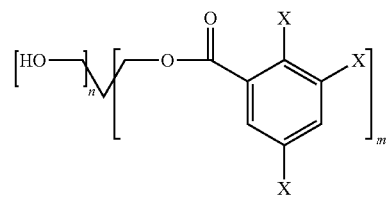

wherein m=4 and n=0, and X is Bromine.

5. A compound having the following formula:

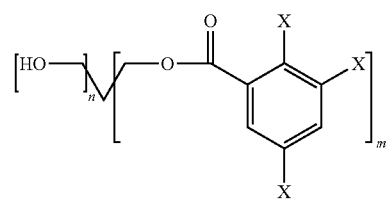

wherein m=4 and n=0, and X is chlorine.

* * * * *